(12) United States Patent  
Gutierrez

(10) Patent No.: US 11,719,678 B2  
(45) Date of Patent: Aug. 8, 2023

(54) ENVIRONMENTAL EMISSION MONITORING SYSTEM WITH GHG EMISSION THRESHOLDING AND RELATED METHOD

(71) Applicant: EAGLE TECHNOLOGY, LLC, Melbourne, FL (US)

(72) Inventor: Guillermo E. Gutierrez, Washington, DC (US)

(73) Assignee: EAGLE TECHNOLOGY, LLC, Melbourne, FL (US)

( * ) Notice: Subject to any disclaimer, the term of this patent is extended or adjusted under 35 U.S.C. 154(b) by 176 days.

(21) Appl. No.: 17/241,468

(22) Filed: Apr. 27, 2021

(65) Prior Publication Data

US 2022/0341907 A1    Oct. 27, 2022

(51) Int. Cl.
```
G01N 33/00      (2006.01)
G01N 21/3504    (2014.01)
G01N 21/359     (2014.01)
```

(52) U.S. Cl.
CPC ..... *G01N 33/0075* (2013.01); *G01N 21/3504* (2013.01); *G01N 21/359* (2013.01); *G01N 2201/129* (2013.01)

(58) Field of Classification Search
CPC .......... G01N 33/0075; G01N 21/3504; G01N 21/359
See application file for complete search history.

(56) References Cited

U.S. PATENT DOCUMENTS

| 9,514,493 | B2 | 12/2016 | Marino |
| 9,719,879 | B1 * | 8/2017 | Tan ............... G01M 3/2892 |
| 9,959,374 | B2 | 5/2018 | Rosti et al. |
| 10,203,311 | B2 * | 2/2019 | Risk ............... G01P 13/02 |

(Continued)

FOREIGN PATENT DOCUMENTS

GB    2574045    11/2019

OTHER PUBLICATIONS

Aistechspace "Thermal Imagery" https://aistechspace.com; https://aistechspace.com/data-services-thermal-imagery; retreived from internet Apr. 12, 2021; pp. 3.

(Continued)

*Primary Examiner* — Bryan Bui  
(74) *Attorney, Agent, or Firm* — Allen, Dyer, Doppelt + Gilchrist, P.A.

(57) ABSTRACT

An environmental emission monitoring system may include satellites configured to sense GHG emissions data for an AOI, and a server. The server may be configured to obtain the sensed GHG emissions data from the satellites, obtain geospatial positions of stationary GHG emitting point sources within the AOI, and generate expected stationary GHG emission data for the stationary GHG emitting point sources within the AOI and based upon the geospatial positions. The server may also be configured to obtain geospatial path data for GHG emitting vehicles moving within the AOI, generate expected vehicle GHG emission data for the GHG emitting vehicles moving within the AOI and based on the geospatial path data, and compare a sum of the expected stationary GHG emission data and expected vehicle GHG emission data with the sensed GHG emissions data to identify any stationary GHG emitting point source and any GHG emitting vehicle outside of a respective GHG emission threshold.

20 Claims, 2 Drawing Sheets

(56) References Cited

U.S. PATENT DOCUMENTS

| | | |
|---|---|---|
| 10,447,383 B1 | 10/2019 | Haas, Jr. et al. |
| 2018/0245935 A1 | 8/2018 | Ba et al. |
| 2022/0205966 A1* | 6/2022 | Althoff .................. G01N 21/33 |

OTHER PUBLICATIONS

Robert Schingler "Carbon Mapper Launches Satellite Program To Pinpoint Methane And CO2 Super Emitters" https://www.planet.com/pulse/carbon-mapper-launches-satellite-program-to-plnpoint-methane-and-co2-super-emitters;0 Apr. 15, 2021 pp. 6.

Li et al. "A Global Analysis of Sentinel-2A, Sentinel-2B and Landsat-8 Data Revisit Intervals and Implications for Terrestrial Monitoring" https://www.mdpi.com/journal/remotesensing; Remote Sens. Sep. 2017, 902; pp. 17.

\* cited by examiner

ENVIRONMENTAL EMISSION MONITORING SYSTEM WITH GHG EMISSION THRESHOLDING AND RELATED METHOD

TECHNICAL FIELD

The present disclosure relates to the field of satellite sensing, and, more particularly, to a greenhouse gas sensing and related methods.

BACKGROUND

With the implementation of the Paris Agreement, the nations of the world are attempting to reduce greenhouse gas (GHG) emissions. Given the global nature of GHG emissions, any verification and enforcement mechanism may necessarily be global in scale. Moreover, physical access for many sites may be impractical or discouraged by the local entities.

One approach to this issue of verification is recently deployed GHG sensing satellite systems. For example, the GHGSAT-C1 system (as available from GHGSat, Inc. of Montreal, Canada) comprises a plurality of low earth orbit (LEO) satellites, which can sense GHG emissions within the atmosphere. This approach may be helpful as it requires no physical access, and can provide periodic updates multiple times a day for a geographical area.

Another approach is installation of terrestrial GHG emissions sensors for stationary point sources, such as, for example, fossil fuel burning power plants. Nevertheless, this approach may also use some physical access for the installation and maintenance during the lifetime of the emission sensor.

SUMMARY

Generally, an environmental emission monitoring system may include a plurality of satellites configured to sense GHG emissions data for an area of interest (AOI), and a server comprising a processor and a memory coupled thereto. The processor may be configured to obtain the sensed GHG emissions data from the plurality of satellites, and obtain geospatial positions of a plurality of stationary GHG emitting point sources within the AOI. The processor may be configured to generate expected stationary GHG emission data for the plurality of stationary GHG emitting point sources within the AOI and based upon the geospatial positions, and obtain geospatial path data for a plurality of GHG emitting vehicles moving within the AOI. The processor may be configured to generate expected vehicle GHG emission data for the plurality of GHG emitting vehicles moving within the AOI and based on the geospatial path data, and compare a sum of the expected stationary GHG emission data and expected vehicle GHG emission data with the sensed GHG emissions data to identify any stationary GHG emitting point source and any GHG emitting vehicle outside of a respective GHG emission threshold.

More specifically, the processor may be configured to generate the expected vehicle GHG emission data based upon respective vehicle types for the plurality of GHG emitting vehicles. In some embodiments, each satellite may comprise a short-wave infrared (SWIR) receiver, for example, for detecting emissions in the AOI.

For example, the processor may be configured to obtain the geospatial path data from one or more of an Automatic Dependent Surveillance-Broadcast (ADS-B) database, an automatic identification system (AIS) database, and a global positioning system (GPS) database.

Also, the processor may be configured to identify any stationary GHG emitting point source and any GHG emitting vehicle outside of the respective GHG emission threshold over time. For example, each GHG emitting vehicle comprises one of an aircraft, a watercraft, and a ground vehicle. In some embodiments, each satellite may comprise a LEO satellite.

Another aspect is directed to a server for environmental emission monitoring. The server may include a processor and a memory coupled thereto and configured to obtain sensed GHG emissions data for an AOI from a plurality of satellites. The processor may be configured to obtain geospatial positions of a plurality of stationary GHG emitting point sources within the AOI, and generate expected stationary GHG emission data for the plurality of stationary GHG emitting point sources within the AOI and based upon the geospatial positions. The processor may be configured to obtain geospatial path data for a plurality of GHG emitting vehicles moving within the AOI, and generate expected vehicle GHG emission data for the plurality of GHG emitting vehicles moving within the AOI and based on the geospatial path data. The processor may be configured to compare a sum of the expected stationary GHG emission data and expected vehicle GHG emission data with the sensed GHG emissions data to identify any stationary GHG emitting point source and any GHG emitting vehicle outside of a respective GHG emission threshold.

Another aspect is directed to a method for environmental emission monitoring. The method may include obtaining sensed GHG emissions data for an AOI from a plurality of satellites, obtaining geospatial positions of a plurality of stationary GHG emitting point sources within the AOI, and generating expected stationary GHG emission data for the plurality of stationary GHG emitting point sources within the AOI and based upon the geospatial positions. The method may include obtaining geospatial path data for a plurality of GHG emitting vehicles moving within the AOI, generating expected vehicle GHG emission data for the plurality of GHG emitting vehicles moving within the AOI and based on the geospatial path data, and comparing a sum of the expected stationary GHG emission data and expected vehicle GHG emission data with the sensed GHG emissions data to identify any stationary GHG emitting point source and any GHG emitting vehicle outside of a respective GHG emission threshold.

DETAILED DESCRIPTION

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout.

Figure 1:
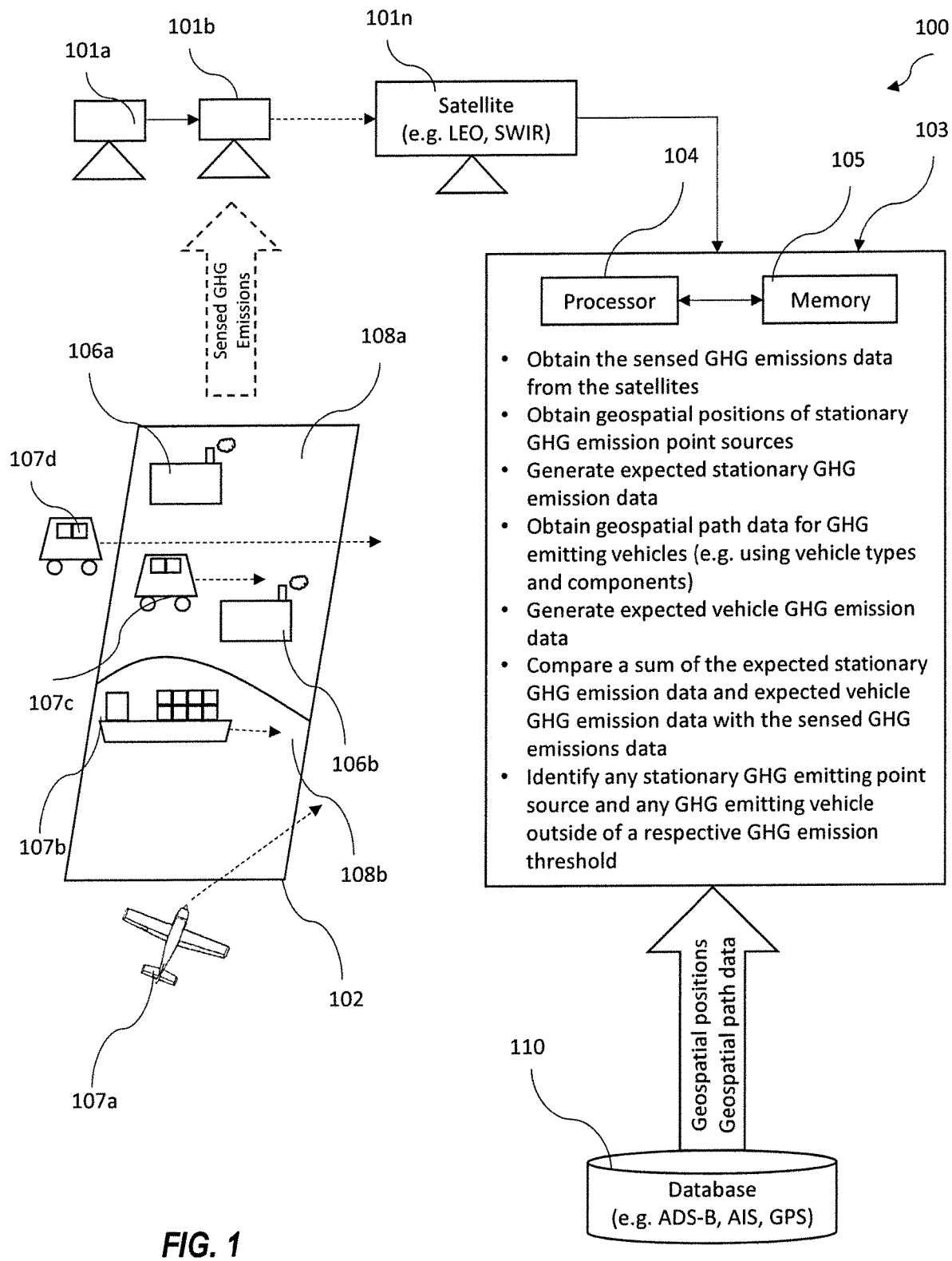
FIG. 1 is a schematic diagram of an environmental emission monitoring system, according to the present disclosure.

Referring initially to FIG. 1, an environmental emission monitoring system 100 according to the present disclosure is now described. The environmental emission monitoring system 100 may provide an approach to global verification and enforcement issues for GHG emissions reduction goals.

The environmental emission monitoring system 100 illustratively includes a plurality of satellites 101a-101n configured to sense GHG emissions data for an AOI 102. Although only one AOI 102 is depicted for illustrative clarity, it should be appreciated that a monitored space may vary depending on the application, and may comprise a large number of AOIs spanning a portion or all of the Earth, including both land regions and water regions. Moreover, a size of the AOI 102 may vary depending on sensing equipment.

In some embodiments, each satellite 101a-101n may comprise a short-wave infrared (SWIR) receiver for detecting emissions in the AOI 102. For example, the plurality of satellites 101a-101n may be provided via one or more of the following systems, as modified by the teachings herein: GHGSat, GOSAT (as available from the Japan Aerospace Exploration Agency), Bluefield 1/2 (as available from Bluefield Technologies Inc. of New York City, N.Y.), MethaneSAT (as available from Blue Canyon Technologies, Inc. of Boulder, Colo.), MERLIN Mission (as available from the European Space Agency), and Scepter Air (as available from Scepter Inc. of Waverly, Tenn.). In some embodiments, each satellite 101a-101n may comprise an LEO satellite. Of course, each satellite 101a-101n may alternatively comprise high Earth orbit (HEO) or medium Earth orbit (MEO) satellites. In some embodiments, the plurality of satellites 101a-101n may comprise a combination of LEO, MEO, and HEO satellites.

The environmental emission monitoring system 100 illustratively includes a server 103 comprising a processor 104 and a memory 105 coupled thereto. In some embodiments, the server 103 comprises resources within a cloud computing platform (e.g., Amazon Web Services or Microsoft Azure), but in other embodiments, the server may comprise one or more standalone computing devices.

The processor 104 is configured to obtain the sensed GHG emissions data from the plurality of satellites 101a-101n. As will appreciated, the processor 104 is configured to access data from the downlink of the plurality of satellites 101a-101n via a software interface from an associated operator. As will be appreciated, the sensed GHG emissions data comprises GHG emission values with geospatial data (e.g., a thermal image of the Earth with colorized GHG emission intensity).

The processor 104 is configured to obtain geospatial positions of a plurality of stationary GHG emitting point sources 106a-106b within the AOI 102. In some embodiments, the processor 104 is configured to store a GHG emission table, including, for each stationary GHG emitting point source 106a-106b, a stationary GHG emitting point source type, a stationary GHG emitting point source geospatial location, and an estimated GHG emission value, for example.

Each of the plurality of stationary GHG emitting point sources 106a-106b may comprise, for example, a power generation plant (e.g., fossil fuel burning), or a manufacturing facility. The processor 104 is configured to generate expected stationary GHG emission data for the plurality of stationary GHG emitting point sources 106a-106b within the AOI 102 and based upon the geospatial positions and the GHG emission table.

In particular, the processor 104 is configured to sort all stationary GHG emitting point sources 106a-106b within the AOI 102. Further, the processor 104 is configured to determine a type and size of each stationary GHG emitting point source 106a-106b in the AOI 102, generate a respective GHG emission value for each stationary GHG emitting point source, and sum all respective GHG emission values within the AOI 102. For example, the processor 104 is configured to determine a given GHG emitting point source as a power plant, and then determine a variant of the power plant for generating the respective GHG emission value. For example, for the power plant GHG emitting point source, $CO_2$ emission values may comprise an instantaneous rate corresponding to 952 million metric tons per anum, 560 million metric tons per anum, and 15 million metric tons per anum for a coal fire power plant, a natural gas power plant, and a petroleum power plant, respectively.

The processor 104 is configured to obtain geospatial path data for a plurality of GHG emitting vehicles 107a-107d moving within the AOI 102. In particular, the geospatial path data may comprise a geospatial location value and a geospatial vector. For example, each GHG emitting vehicle 107a-107d comprises one of an aircraft 107a, a watercraft 107b, and a ground vehicle 107c-107d. As illustrated, the AOI 102 comprises an upper land portion 108a where the stationary GHG emitting point sources 106a-106b and the ground vehicles 107c-107d are located, and a lower water portion 108b where the watercraft 107b is located.

Also, for example, the processor 104 may be configured to obtain the geospatial path data from a database 110. The database 110 may comprise one or more of an ADS-B database (for aircraft 107a, e.g., Opensky Network, Aireon, ESA PROVA-V, and Spire Global), an AIS database (for watercraft 107b, e.g., exactEarth, Aerial Maritime), and a GPS database (ground vehicles 107c-107d, e.g., delivery truck fleet GPS database).

The processor 104 is configured to generate expected vehicle GHG emission data for the plurality of GHG emitting vehicles 107a-107d moving within the AOI 102 and based on the geospatial path data. The processor 104 is configured to determine a type and size of each GHG emitting vehicle 107a-107d, and generate a respective GHG emission value (e.g. emission rate) for each GHG emitting vehicle 107a-107d. As with the stationary GHG emitting point sources 106a-106b, the processor 104 is configured to store the expected GHG emission values in the GHG emission table.

In particular, the processor 104 is configured to generate the expected vehicle GHG emission data based upon respective vehicle types for the plurality of GHG emitting vehicles 107a-107d. For example, the processor 104 is configured to determine a given GHG emitting vehicle as a jet aircraft, and then determine a variant of the aircraft for generating the respective GHG emission value. In some embodiments, such as those using the ADS-B database, the propulsion systems of each GHG emitting vehicle 107a-107d (aircraft 107a) are known, and the processor 104 is configured to generate the expected vehicle GHG emission data, further based upon the propulsion system type, providing greater granularity and accuracy.

In some embodiments, the processor 104 is configured to evaluate a plurality of vehicle parameters to generate the expected vehicle GHG emission data. For example, the plurality of vehicle parameters may include vehicle manufacturer, vehicle propulsion type (e.g., turbine, propeller based, electric, internal combustion engine), vehicle component manufacturer (e.g., turbine engine manufacturer), vehicle owner/operator, vehicle speed, and vehicle load (e.g., container ship, oil tanker, passage jet, cargo jet). Again, as with the stationary GHG emission point sources 106a-106b, the processor 104 is configured to sort all GHG emitting vehicles 107a-107d within the AOI 102, determine a type of each GHG emitting vehicle in the AOI, generate a respective GHG emission value for each GHG emitting vehicle (using the plurality of vehicle parameters), and sum all respective GHG emission values within the AOI.

The processor 104 is configured to compare a sum of the expected stationary GHG emission data and expected vehicle GHG emission data with the sensed GHG emissions data to identify any stationary GHG emitting point source 106a-106b and any GHG emitting vehicle 107a-107d outside of a respective GHG emission threshold. In the ideal situation, the sum of the expected stationary GHG emission data and the expected vehicle GHG emission data, and the sensed GHG emissions data should be substantially identical (i.e. ±5%). In particular, the processor 104 is configured to flag the stationary GHG emitting point sources 106a-106b and the GHG emitting vehicles 107a-107d in the AOI 102 when the sensed GHG emissions data deviates from the expected stationary GHG emission data (e.g., exceeding the ±5% threshold). The processor 104 is configured to iteratively evaluate each AOI 102 in the monitored area, and may be do so periodically. As will be appreciated, those AOIs 102 that are flagged can be set aside for further satellite based evaluation in a typical tipping and queuing regime.

Also, the processor 104 is configured to identify any stationary GHG emitting point source 106a-106b and any GHG emitting vehicle 107a-107d outside of the respective GHG emission threshold over time. For example, the processor 104 is configured to generate time based reports, showing the number of times and when the AOI 102 is flagged.

Although not depicted, some embodiments of the environmental emission monitoring system 100 may include other airborne GHG sensors in communication with the server 103, such as carried by a fixed wing aircraft or an unmanned aerial vehicle (UAV). In one embodiment, the plurality of satellites 101a-101n first tip the AOI 102 for further monitoring, and then, a UAV with GHG sensors is tasked to provide additional data on AOIs 102 in the queue. Moreover, the environmental emission monitoring system 100 may also include terrestrial GHG sensors in communication with the server 103. Of course, in these embodiments, the processor 104 is configured to generate the expected vehicle GHG emission data further based upon the additional data streams.

Moreover, the processor 104 is configured to extrapolate future positions of the plurality of GHG emitting vehicles 107a-107d moving within and outside the AOI 102. In the illustrative example, the processor 104 is configured to account for the GHG emitting vehicle 107a moving into the AOI 102 over time and project its exit. Also, the processor 104 is configured to account for the GHG emitting vehicle 107d moving into the AOI 102 and exiting the AOI over time. Helpfully, the processor 104 is configured to generate the expected vehicle GHG emission data over time more accurately, accounting for entry and departure of GHG emitting vehicles 107a.

Moreover, the processor 104 is configured to generate multiple layers of the expected vehicle GHG emission data. In particular, for a given AOI 102, the processor 104 is configured to generate the expected vehicle GHG emission data for only the plurality of GHG emitting vehicles 107a-107d or only the plurality of stationary GHG emitting point sources 106a-106b. Moreover, the processor 104 is configured to generate filtered data reports and views based upon one or more the plurality of vehicle parameters. For example, the processor 104 may generate expected vehicle GHG emission data for only jet turbine aircraft in the given AOI 102, or for only all Boeing aircraft in the AOI.

Advantageously, the environmental emission monitoring system 100 may provide for remote monitoring of actual GHG emissions. Moreover, the environmental emission monitoring system 100 may flag emissions data that deviates from expected values, which provides an approach to applications that demand global GHG emissions monitoring. Moreover, the environmental emission monitoring system 100 may provide for accurate evaluation of GHG emissions due to vehicular traffic and stationary point sources, enabling on the fly investigation and monitoring. Moreover, while typical GHG emission approaches have been directed to stationary point sources, the environmental emission monitoring system 100 leverages data fusion to track and monitor mobile GHG point sources.

Figure 2:
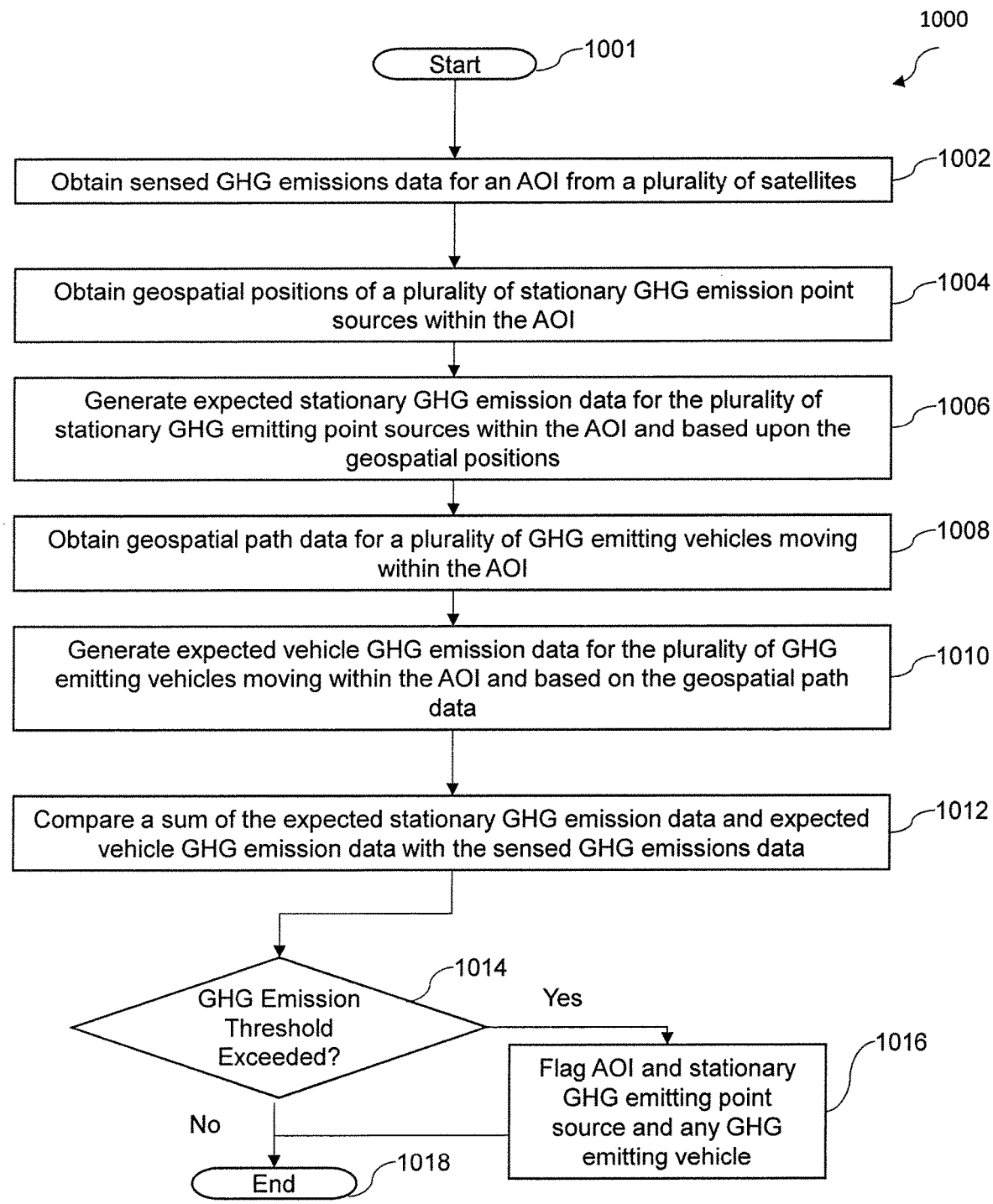
FIG. 2 is a flowchart illustrating a method for environmental emission monitoring, according to the present disclosure.

Referring now additionally to FIG. 2, a method for environmental emission monitoring according to the present disclosure is now described with reference to a flowchart 1000, which begins at Block 1001. The method illustratively comprises obtaining sensed GHG emissions data for an AOI 102 from a plurality of satellites 101a-101n (Block 1002), obtaining geospatial positions of a plurality of stationary GHG emitting point sources 106a-106b within the AOI 102 (Block 1004), and generating expected stationary GHG emission data for the plurality of stationary GHG emitting point sources within the AOI and based upon the geospatial positions (Block 1006). The method includes obtaining geospatial path data for a plurality of GHG emitting vehicles 107a-107d moving within the AOI 102 (Block 1008), and generating expected vehicle GHG emission data for the plurality of GHG emitting vehicles moving within the AOI and based on the geospatial path data (Block 1010).

The method illustratively comprises comparing a sum of the expected stationary GHG emission data and expected vehicle GHG emission data with the sensed GHG emissions data to identify any stationary GHG emitting point source 106a-106b and any GHG emitting vehicle 107a-107d outside of a respective GHG emission threshold. (Blocks 1012, 1014, 1016, 1018). In particular, the processor 104 is configured to determine a difference value between the sum of the expected stationary GHG emission data and the expected vehicle GHG emission data with the sensed GHG emissions data. (Block 1014). If the difference value exceeds a threshold (e.g., ±5%), the stationary GHG emitting point sources 106a-106b and the GHG emitting vehicles 107a-107d within the AOI 102 are flagged (Blocks 1016, 1018). In other words, alerts may be sent to the appropriate governing authority for follow-up if thresholds are exceeded. It should be appreciated that Blocks 1002-1016 are iteratively repeated until all AOIs have been evaluated.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

The invention claimed is:

1. An environmental emission monitoring system comprising:
a plurality of satellites configured to sense greenhouse gas (GHG) emissions data for an area of interest (AOI); and
a server comprising a processor and a memory coupled thereto and configured to
obtain the sensed GHG emissions data from the plurality of satellites,
obtain geospatial positions of a plurality of stationary GHG emitting point sources within the AOI,
generate expected stationary GHG emission data for the plurality of stationary GHG emitting point sources within the AOI and based upon the geospatial positions,
obtain, from at least one database, geospatial path data for a plurality of GHG emitting vehicles moving within the AOI,
generate expected vehicle GHG emission data for the plurality of GHG emitting vehicles moving within the AOI and based on the geospatial path data, and
compare a sum of the expected stationary GHG emission data and expected vehicle GHG emission data with the sensed GHG emissions data to identify any stationary GHG emitting point source and any GHG emitting vehicle outside of a respective GHG emission threshold.

2. The environmental emission monitoring system of claim 1 wherein the processor is configured to generate the expected vehicle GHG emission data based upon respective vehicle types for the plurality of GHG emitting vehicles.

3. The environmental emission monitoring system of claim 1 wherein each satellite comprises a short-wave infrared (SWIR) receiver for detecting emissions in the AOI.

4. The environmental emission monitoring system of claim 1 wherein the at least one database comprises an Automatic Dependent Surveillance-Broadcast (ADS-B) database.

5. The environmental emission monitoring system of claim 1 wherein the at least one database comprises an automatic identification system (AIS) database.

6. The environmental emission monitoring system of claim 1 wherein the processor is configured to identify any stationary GHG emitting point source and any GHG emitting vehicle outside of the respective GHG emission threshold over time.

7. The environmental emission monitoring system of claim 1 wherein each GHG emitting vehicle comprises one of an aircraft, a watercraft, and a ground vehicle.

8. The environmental emission monitoring system of claim 1 wherein the at least one database comprises a global positioning system (GPS) database.

9. The environmental emission monitoring system of claim 1 wherein each satellite comprises a low Earth orbit (LEO) satellite.

10. A server for environmental emission monitoring, the server comprising:
a processor and a memory coupled thereto and configured to
obtain sensed greenhouse gas (GHG) emissions data for an area of interest (AO') from a plurality of satellites,
obtain geospatial positions of a plurality of stationary GHG emitting point sources within the AOI,
generate expected stationary GHG emission data for the plurality of stationary GHG emitting point sources within the AOI and based upon the geospatial positions,
obtain, from at least one database, geospatial path data for a plurality of GHG emitting vehicles moving within the AOI,
generate expected vehicle GHG emission data for the plurality of GHG emitting vehicles moving within the AOI and based on the geospatial path data, and
compare a sum of the expected stationary GHG emission data and expected vehicle GHG emission data with the sensed GHG emissions data to identify any stationary GHG emitting point source and any GHG emitting vehicle outside of a respective GHG emission threshold.

11. The server of claim 10 wherein the processor is configured to generate the expected vehicle GHG emission data based upon respective vehicle types for the plurality of GHG emitting vehicles.

12. The server of claim 10 wherein each satellite comprises a short-wave infrared (SWIR) receiver for detecting emissions in the AOI.

13. The server of claim 10 wherein the at least one database comprises an Automatic Dependent Surveillance-Broadcast (ADS-B) database.

14. The server of claim 10 wherein the at least one database comprises an automatic identification system (AIS) database.

15. The server of claim 10 wherein the processor is configured to identify any stationary GHG emitting point source and any GHG emitting vehicle outside of the respective GHG emission threshold over time.

16. The server of claim 10 wherein each GHG emitting vehicle comprises one of an aircraft, a watercraft, and a ground vehicle.

17. The server of claim 10 wherein the at least one database comprises a global positioning system (GPS) database.

18. A method for environmental emission monitoring, the method comprising:
obtaining sensed greenhouse gas (GHG) emissions data for an area of interest (AO') from a plurality of satellites;
obtaining geospatial positions of a plurality of stationary GHG emitting point sources within the AOI;
generating expected stationary GHG emission data for the plurality of stationary GHG emitting point sources within the AOI and based upon the geospatial positions;
obtaining, from at least one database, geospatial path data for a plurality of GHG emitting vehicles moving within the AOI;
generating expected vehicle GHG emission data for the plurality of GHG emitting vehicles moving within the AOI and based on the geospatial path data; and
comparing a sum of the expected stationary GHG emission data and expected vehicle GHG emission data with the sensed GHG emissions data to identify any stationary GHG emitting point source and any GHG emitting vehicle outside of a respective GHG emission threshold.

19. The method of claim 18 wherein the generating of the expected vehicle GHG emission data is based upon respective vehicle types for the plurality of GHG emitting vehicles.

20. The method of claim 18 wherein each satellite comprises a short-wave infrared (SWIR) receiver for detecting emissions in the AOI.

\* \* \* \* \*